United States Patent [19]

Himel et al.

[11] 4,286,020

[45] Aug. 25, 1981

[54] IN-FLIGHT ENCAPSULATION OF PARTICLES

[75] Inventors: Chester M. Himel, Athens, Ga.; Nathan F. Cardarelli, Barberton, Ohio

[73] Assignee: Environmental Chemicals, Inc., Wauconda, Ill.

[21] Appl. No.: 149,982

[22] Filed: May 15, 1980

Related U.S. Application Data

[63] Continuation of Ser. No. 922,171, Jul. 5, 1978, abandoned.

[51] Int. Cl.³ .......................... B32B 5/16; B01J 13/00; B29C 6/00; B29C 13/00

[52] U.S. Cl. .................................... 428/407; 252/316; 264/4; 264/13

[58] Field of Search ...................... 252/316; 264/4, 13; 428/407

[56] References Cited

U.S. PATENT DOCUMENTS

| | | | |
|---|---|---|---|
| 3,007,887 | 11/1961 | Essig | 526/16 |
| 3,265,629 | 8/1966 | Jensen | 424/33 |
| 3,336,155 | 8/1967 | Rowe | 252/316 |
| 3,544,500 | 12/1970 | Osmond et al. | 252/316 |
| 3,639,306 | 2/1972 | Sternberg et al. | 428/407 |
| 3,806,464 | 4/1974 | Matrick et al. | 252/316 |
| 3,830,750 | 8/1974 | Wellman | 252/316 |
| 3,872,023 | 3/1975 | Baum et al. | 252/316 |
| 4,071,653 | 1/1978 | Boessler et al. | 428/407 |
| 4,107,071 | 8/1978 | Bayless | 252/316 |
| 4,187,194 | 2/1980 | Wellman et al. | 264/4 |
| 4,211,668 | 7/1980 | Tate | 252/316 |

*Primary Examiner*—William R. Dixon, Jr.

*Attorney, Agent, or Firm*—Oldham, Oldham, Hudak & Weber Co.

[57] ABSTRACT

A method and composition for the in-flight encapsulation of particles such as insecticides, herbicides, molluscicides, acaricides, fungicides, nutrients, pheromenes, odorants, fragrances, attractants, repellants, trace elements, and the like. The composition comprises, by weight, from 1 to 40 percent of said particles, from 0.3 to 25 percent of a film-forming polymer and from 35 to 99 percent of a solvent which renders said polymers soluble. Often, other compounds may be added to impart desirable properties such as a second film-forming polymer, crosslinking agents, film modifying agents, and adhesives to improve adhesion to a target. The particle may be in a true solution suspended or emulsified through the action of surfactants and/or emulsifying agents. The film-forming polymer is selected from the class consisting of polyvinyl ethers, polyvinyl acetate, and interpolymers of alpha-beta olefinically unsaturated carboxylic acids and N-methylol acrylic amides, as set forth in U.S. Pat. No. 3,007,887. Upon ejection from a spray apparatus and during flight through the intervening atmosphere, the solution rapidly loses the solvent component via evaporation, coacervation occurs, and a polymeric membrane forms about the particle. Control of the encapsulated particle size can be achieved through selection of the spray system and of the non-volatiles in the spray at the moment of droplet formation.

80 Claims, 4 Drawing Figures

IN-FLIGHT ENCAPSULATION OF PARTICLES

CROSS-REFERENCE

This is a continuation of pending application Ser. No. 922,171 filed July 5, 1978 for IN-FLIGHT ENCAPSULATION OF PARTICLES, now abandoned.

BACKGROUND OF THE INVENTION

The present invention relates to a composition of a self-encapsulating polymeric-containing solution and a process for the in-flight encapsulation of particles such as insecticides, fungicides, herbicides, etc., contained therein. More specifically, the present invention relates to the in-flight encapsulation of said particles during passage between the egress of a spray apparatus and a target.

Heretofore, the encapsulation of a chemical substance within an enveloping polymeric membrane has been well recognized by the art. For example, U.S. Pat. Nos. 3,242,051, 3,265,629, 3,575,882, and 3,607,776 all relate to processes dependent upon phase separation and polycondensation reactions. Specifically, U.S. Pat. No. 3,242,051 relates to preparing a solution of a liquid phase-forming micromolecular polymer in a first non-aqueous liquid, dispersing in said solution a plurality of individual discreet particles, adding a second liquid soluble in the first liquid, but not soluble with regard to said micromolecular polymer, whereby phase separation is induced and precoats the dispersed particles, settling the polymer-rich precoat, separating the precoated particles, suspending the precoated particles in an aqueous solution of a gel, and using phase separation so as to cause the formation of a colloidal-enriched phase and the encapsulation of each of these suspended precoated particles, and cooling.

U.S. Pat. No. 3,265,629 is similar but relates to the application of two coatings to the particles, namely a solid lipid and a polymer.

U.S. Pat. No. 2,648,609 relates to an air suspension technique wherein a sugar solution is sprayed onto a suspended item such as candy, gum, etc. Another technique heretofore utilized is the utilization of charging a first solution with ions so that the solution exhibits a specific charge, applying an opposite charge to a second solution, and then coating the first solution with the second solution via air flow.

U.S. Pat. No. 3,202,533 relates to the encapsulation of liquids by the use of a fluidized bed wherein the fluidized liquid is frozen and spray coated.

Common to all such above-described inventions and prior art processes is the utilization of multiple compounds or compositions of matter as well as the necessity of processing the encapsulated or micro-encapsulated article prior to usage or application. Moreover, costly and complex processing equipment as well as difficult technology is required to produce articles of a defined size and to meet mandatory environmental controls or regulations.

In contrast, the present invention relates to but a single self-encapsulating polymeric containing solution. Moreover, the invention pertains to encapsulation of a particle phase via a polymer through in-flight encapsulation; that is, during the passage from the spraying or ejection equipment to the target substance or area, including an agricultural or forested area.

SUMMARY OF THE INVENTION

It is, therefore, an object of the present invention to provide a composition and process for the in-flight encapsulation of particles.

It is another object of the present invention to provide for the in-flight encapsulation of particles, as above, wherein said composition comprises generally a film-forming polymer in a solvent system for solubilizing said polymer, and any desired particles which may be soluble or dispersed in the solvent medium.

It is a further object of the present invention to provide for the in-flight encapsulation of particles, as above, wherein upon ejection from a spray apparatus and during flight through the intervening earth's atmosphere, the solution rapidly loses the solvent component through evaporation with coacervation occurring and resulting in the formation of a polymer membrane about the particle.

It is a further object of the present invention to provide for the in-flight encapsulation of particles, as above, wherein said particle is encapsulated by said polymer upon the evaporation of some or most, if not all, of the solvent in the process of passage of said particle between an ejector or a spray apparatus and a target.

It is an additional object of the present invention to provide for the in-flight encapsulation of particles, as above, wherein said particles are very small so that a microencapsulated product is produced.

It is a still further object of the present invention to provide for the in-flight encapsulation of particles, as above, wherein said encapsulated product is of fairly uniformed particle size.

It is a still further object of the present invention to provide for the in-flight encapsulation of particles, as above, wherein an outer polymer membrane exists about an inner particle core.

It is a still additional object of the present invention to provide for the in-flight encapsulation of particles, as above, wherein, due largely to the uniform product size, target specificity can be incorporated into the in-flight system.

It is yet another object of the present invention to provide for the in-flight encapsulation of particles, as above, wherein said encapsulated particle can be insecticides, acaricides, fungicides, herbicides, nutrients, trace minerals, nematicides, molluscicides, pheromenes, odorants, fragrances, attractants, repellants, and any other desired particle.

It is yet another object of the present invention to provide for the in-flight encapsulation of particles, as above, wherein the leaching of said particle on a target instead of occurring in a matter of minutes or hours can range from a day to a period of months.

It is yet another object of the present invention to provide for the in-flight encapsulation of particles, as above, wherein crosslinking agents may be added to said solution to control the leaching time period.

It is yet another object of the present invention to provide for the in-flight encapsulation of particles, as above, wherein various adhesive and film-modifying agents may be added to said solution so that improved adhesion of said encapsulated product to said target occurs.

These and other objects of the present invention will become apparent from the following preferred embodiment of the invention.

In general, a process for the in-flight encapsulation of particles, comprises the steps of: preparing a self-encapsulating polymeric-containing solution; said solution comprising by weight from about 0.3 percent to about 25 percent of a polymer, from about 35 percent to about 99 percent of a solvent, said solvent being a compound which will solubilize said polymer, and from about 1 percent to about 40 percent of the particles, said particle being immiscible with said solvent; said polymer selected from the class consisting of (a) polyvinyl acetate, (b) a polyvinyl ether wherein said repeating unit has from 2 to 10 carbon atoms, (c) an acrylic polymer or a copolymer made from monomers having the formula

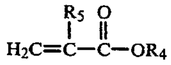

where $R_4$ is hydrogen or an alkyl, cycloalkyl, aryl, or aralkyl having from 1 to 30 carbon atoms and $R_5$ is hydrogen or an alkyl, cycloalkyl, aryl, or aralkyl having from 1 to 12 carbon atoms, (d) the salt of (1) an interpolymer having the structure

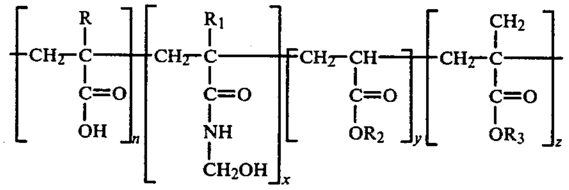

wherein R and $R_1$ are members of the group consisting of hydrogen and methyl; $R_2$ is a member of the group consisting of methyl, ethyl, propyl and butyl; $R_3$ is a member of the group consisting of methyl and ethyl; n represents from 3 to 12 weight percent based on the combined weight of n, x, y and z; x represents from 8 to 25 weight percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of $n+x+y+z$ is always exactly 100 and the groups n, x, y and z are present in a heterogeneous relative position, and (2) a member of the group consisting of ammonia, hydrazine, a low boiling primary aliphatic amine and a low boiling second aliphatic amine, said salt being soluble in water in the pH range of from about 5 to about 8, and (e) combinations thereof; spraying said solution from a spray apparatus and, immediately thereafter, in-flight encapsulating said solution by evaporating said solvent so that said polymer encapsulates said particle.

Generally, a self-encapsulating polymeric-containing solution comprises, by weight, based upon the total weight of said solution from about 0.3 percent to about 25 percent of a polymer, from about 35 percent to about 99 percent of a solvent, and from 1 percent to about 40 percent of a particle; said polymer selected from the class consisting of (a) a polyvinyl acetate, (b) a polyvinyl ether wherein said repeating unit has from 3 to 10 carbon atoms, (c) an acrylic polymer or a copolymer made from monomers having the formula

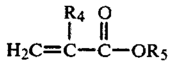

where $R_4$ is hydrogen or an alkyl, cycloalkyl, aryl, or aralkyl having from 1 to 30 carbon atoms and $R_5$ is hydrogen or an alkyl, cycloalkyl, aryl, or aralkyl having from 1 to 12 carbon atoms, (d) the salt of (1) an interpolymer having the structure

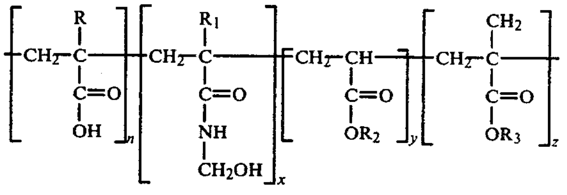

where R and $R_1$ are members of the group consisting of hydrogen and methyl; $R_2$ is a member of the group consisting of methyl, ethyl, propyl and butyl; $R_3$ is a member of the group consisting of methyl and ethyl; n represents from 3 to 12 weight percent based on the combined weight of n, x, y and z; x represents from 8 to 25 weight percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of $n+x+y+z$ is always exactly 100 and the groups n, x, y and z are present in a heterogeneous relative position, and (2) a member of the group consisting of ammonia, hydrazine, a low boiling primary aliphatic amine and a low boiling second aliphatic amine, said salt being soluble in water in the pH range of from about 5 to about 8, and (e) combinations thereof; said particle being soluble or dispersible in said solvent; and said solvent being a compound in which said polymer is soluble.

Additionally, an encapsulated particle comprises: a particle, said particle coated with a film-forming polymer; said polymer selected from the class consisting of (a) a polyvinyl acetate, (b) a polyvinyl ether wherein said repeating unit has from 3 to 10 carbon atoms, (c) an acrylic polymer or a copolymer made from monomers having the formula

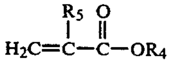

where $R_4$ is hydrogen or an alkyl, cycloalkyl, aryl, or aralkyl having from 1 to 10 carbon atoms and $R_5$ is hydrogen or an alkyl, cycloalkyl, aryl, or aralkyl having from 1 to 12 carbon atoms, (d) the salt of (1) an interpolymer having the structure

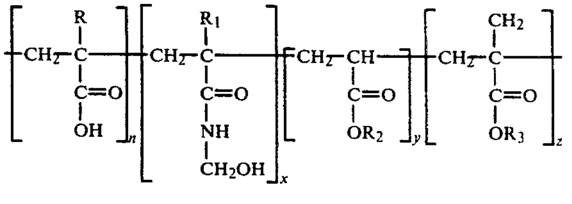

wherein R and $R_1$ are members of the group consisting of hydrogen and methyl; $R_2$ is a member of the group consisting of methyl, ethyl, propyl and butyl; $R_3$ is a member of the group consisting of methyl and ethyl; n represents from 3 to 12 weight percent based on the combined weight of n, x, y and z; x represents from 8 to 25 weight percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of n+x+y+z is always exactly 100 and the groups n, x, y and z are present in a heterogeneous relative position, and (2) a member of the group consisting of ammonia, hydrazine, a low boiling primary aliphatic amine and a low boiling second aliphatic amine, said salt being soluble in water in the pH range of from about 5 to about 8, and (e) combinations thereof.

IN THE DRAWINGS

PREFERRED EMBODIMENT OF THE INVENTION

Figure 1:
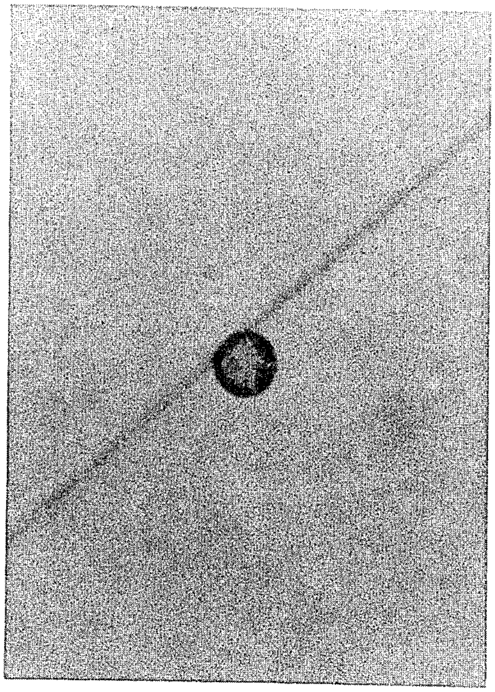
FIG. 1 is a photograph of an encapsulated particle, according to the present invention, wherein a polymeric film is shown about the particle and the film is adhered to a glass strand.

The concepts of the present invention relate to a composition and process with regard to the in-flight encapsulation of particles. Numerous applications exist through conventional ejection equipment such as conventional spraying apparatus to apply encapsulated particles for various utilities, for example, public health protection, agricultural applications, and any other area or field in which the encapsulation of particles, especially micro-encapsulation, is desired. By the term "in-flight encapsulation" it is meant that the particle is covered, surrounded, coated, or encapsulated by a film-forming polymer by a coacervation process during or between the passage from an ejector or a spraying apparatus to a desired target, material, area, or the like. Moreover, the encapsulated material of the present invention results in a controlled release of the particle through a leaching mechanism so that in effect a slow release of the particle is achieved from a matter of a day or two to several weeks or months.

The self-encapsulating polymeric-containing solution comprises a film-forming polymer in a solvent in which the polymer is soluble, and the particle itself. Therefore, the polymeric-containing solution exists as a particle either dissolved or dispersed in the solvent-polymer phase. At times, a three-phase system can be used in which the solvent constitutes the third phase. On a weight basis, the total amount of polymer utilized ranges from about 0.3 percent to about 25 percent, with from about 2 to about 18 percent being desirable, and from 4 to 13 percent being preferred. Often times, instead of a single film-forming polymer, two or even three types of polymers can be utilized. The amount of solvent ranges from about 35 percent to about 99 percent with from about 50 to about 90 being preferred. The amount of particle ranges from about 1 percent to about 40 percent with from about 5 to about 30 percent being preferred. Naturally, as will be better understood by referring to the examples in the specification, the various components or compounds can be varied to achieve specific changes in properties of the final product; that is, the encapsulated particle. Additionally, various adhesive agents, crosslinking agents, emulsifying agents, and other additives may be added to further modify either the process or the end product properties.

Suitable polymers for use in the present invention relate to film-forming polymers which are capable of encapsulating the particle by coacervation and which form a polymeric film about the particle. Such a specific polymer is polyvinyl acetate having a molecular weight range of from about 10,000 to about 100,000. Another suitable and desired polymer is the polyvinyl ethers wherein the repeating hydrocarbon group is an alkyl having from 2 to 10 carbon atoms, preferably 2 carbon atoms, and with the polymer having a molecular weight of from about 10,000 to about 100,000.

A preferred polymer of the present invention relates to carboxylated acrylic polymers and copolymers such as those made from monomers having the formula

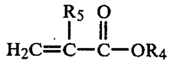

where $R_4$ is a hydrogen radical or a hydrocarbon group having from 1 to 30 carbon atoms and $R_5$ is a hydrogen radical or a hydrocarbon group having from 1 to 12 carbon atoms, both hydrocarbon groups selected from the class consisting of alkyl, cycloalkyl, aryl, and aralkyl. Desirably, $R_4$ is an alkyl having from 1 to 4 carbon atoms and preferably is hydrogen. $R_5$, desirably, has from 1 to 3 carbon atoms and, preferably, either has 1 carbon atom or is hydrogen. By carboxylated, it is meant that a substantial number of the pendant groups of the polyacrylate contains carboxyl groups. Moreover, by copolymers, it is meant that the polymer may be made from 2 or more monomers having the above formulation. A preferred polymer is made from methacrylate monomers with a preferred polymer being made from acrylic acid monomers. The molecular weight of the carboxylated acrylic polymers generally ranges from 10,000 to 600,000 with a preferred range being from about 30,000 to about 300,000.

A higher preferred polymeric compound of the present invention are the salts of interpolymers of alpha-beta olefinically unsaturated carbonyl monomers which contain N-methylol acrylic amides as set forth in U.S. Pat. No. 3,007,887, which is hereby fully incorporated by reference with regard to the preparation, content and description of the inner polymers. Generally, the interpolymer has the following structure:

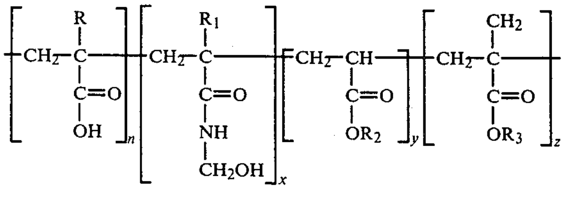

where R and $R_1$ are members of the group consisting of hydrogen and methyl; $R_2$ is a member of the group consisting of methyl, ethyl, propyl and butyl; $R_3$ is a member of the group consisting of methyl and ethyl; n represents from 3 to 12 weight percent based on the combined weight of n, x, y and z; x represents from 8 to 25 weight percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of $n+x+y+z$ is always exactly 100 and the groups n, x, y and z are present in a heterogeneous relative position. The interpolymer is converted from an alcohol solution to water solutions by the addition of water having neutralizing agents such as ammonia, a hydrazine, or a low-boiling amine to the alcoholic solution of the interpolymer followed by an azeotropic distillation which removes the last traces of the alcohol and the excess neutralizing agent. The final aqueous solution of the polymer salt is preferably in the range of pH 5–8 and more preferably in the range of pH 6–7 with a total solids content of from about 2 to 40 percent by weight and preferably from about 5 to about 30 percent by weight of polymer in water.

The polymers embodied in this invention are those compositions comprising from 45 to 89 parts by weight of a lower acrylic acid ester, from 0 to 44 parts by weight of a lower methacrylic acid ester, from 3 to 12 parts by weight of an alpha-beta olefinically unsaturated carboxylic acid having a terminal $CH_2{=}C{<}$ group and having from 3 to 4 carbon atoms and from 8 to 25 parts by weight of an N-methylol alpha-beta olefinically unsaturated carboxylic acid amide having a terminal $CH_2{=}C{<}$ group and having from 4 to 5 carbon atoms.

The lower acrylic acid esters useful in this invention include those in which $R_2$ in the above formula is an aliphatic hydrocarbon group having from 1 to 4 carbon atoms such as methyl acrylate, ethyl acrylate, n-propyl acrylate, isopropyl acrylate, n-butyl acrylate, isobutyl acrylate and secondary butyl acrylate. The most preferred lower acrylic acid esters are methyl acrylate and ethyl acrylate. The lower acrylate acid esters are useful in the range of from about 45 to about 89 weight percent based on the weight of the other monomers.

The lower methacrylic acid esters useful in this invention include those in which $R_3$ in the above formula is an aliphatic hydrocarbon group having from 1 to 2 carbon atoms such as methyl methacrylate and ethyl methacrylate. The preferred methacrylic acid ester is methyl methacrylate. The lower methacrylate acid esters are useful in the range of from about 0 to about 44 weight percent based on the weight of the other monomers.

The alpha-beta olefinically unsaturated carboxylic acids embodied in this invention include acrylic acid and methacrylic acid. The alpha-beta olefinically unsaturated carboxylic acids are useful in the range of from about 3 to about 12 weight percent based on the weight of the other monomers.

The N-methylol acrylic amides embodied in this invention include N-methylol acrylamide and N-methylol methacrylamide. The most preferred N-methylol acrylic amide is N-methylol acrylamide. The N-methylol acrylic amides are useful in the range of from about 8 to about 25 weight percent based on the weight of the other monomers.

The molecular weight of the polymer represented by the above interpolymer structure generally ranges from about 20,000 to about 1,000,000, with a weight of from about 30,000 to about 250,000 being preferred.

Specific examples of the above interpolymers include Carboset XL11 (molecular weight of about 45,000), Carboset 514 (molecular weight of about 30,000), Carboset 515 (molecular weight of about 70,000, Carboset 525 (molecular weight of about 260,000), Carboset 526 (molecular weight of 300,000), all manufactured by the B. F. Goodrich Company. Generally, the higher the identification number, the higher the molecular weight of the particular interpolymer.

The solvent may be any solvent which will solubilize the above polymers. Generally, water and alkanols having from 1 to 5 carbon atoms, and combinations thereof, may be utilized. Examples of specific alcohols include methanol, propanol, isopropanol, butanol, isobutanol, pentanol, etc., with ethanol being preferred. Other suitable solvents include acetone, diisobutyl ketone, methyl ethyl ketone, dioxane, and methylene chloride. Moreover, other solvents may be used in which the particle is generally soluble or emulsifiable therein.

The particle is usually a solid. However, in some instances, the particle can be a liquid. Regardless of whether the particle is a solid or a liquid, it can be any compound which, as part of the self-encapsulating solution, can be ejected or sprayed by either known or conventional ejecting or spraying apparatus. Although the particles may be of any size so long as they can be sprayed or ejected by an apparatus, they are desirably small to facilitate in the ease of ejecting or spraying the solution or, generally, due to their nature of application. For example, at least 90 percent of the particles having a size ranging from less than 1 micron to 200 may be utilized, although, generally, they are from a much smaller range as from about 1 to about 100 microns. For insecticides, odorants, etc., the application of particles smaller than 100 microns, as from 1 to 50 microns, are preferred.

Naturally, it is desirable that the particle, the solvent, and the polymer be compatible with each other in that they lack chemical interaction.

The particle compounds include nutrients such as fertilizers or vital trace minerals, insecticides, acaricides, nematicides, molluscicides, herbicides, fungicides, pheromenes, odorants, fragrances, attractants, repellants, and innocuous materials for scientific effort, keyed to elucidating spray equipment design, spray effects depending upon environmental influences, and the like, or other materials where rapid and controlled delivery to a given target is desired. Specific examples of these classes of particles are set forth below.

| Trace Nutrients | |
|---|---|
| Zinc chloride | Boric acid |
| Zinc sulfate | Sodium borate |
| Ferric chloride | Sodium selenate |
| Ferric sulfate | Cobalt sulfate |
| Copper sulfate | Sodium molybdate |
| Copper oxychloride | Manganese chloride |

Insecticides and Acaricides

O,O-diethyl-O-p-nitrophenyl phosphorothiaote (Parathion)
O,O-dimethyl-O-p-nitrophenyl phosphorothioate (Methyl parathion)
O,O-dimethyl-O-(3-methyl-4-nitrophenyl)phosphorothioate (Sumithion)
O,O-diethyl-O-(2-isopropyl-6-methyl-5-pyrimidinyl) phosphorothioate (Diazinon)

-continued

| |
|---|
| O,O-dimethyl-O-[3-methyl-4-(methylthio)phenyl]phosphorothioate (Fenthion) |
| Pyrethrin-piperonyl butoxide |
| 1-naphthyl methylcarbamate (Carbaryl) |
| 2-(1-methylethoxy)phenol methylcarbamate (Baygon, manufactured by Chemagro |
| 2-methyl-2-(methylthio)propionaldehyde-O-(methyl carbamoyl) oxime (Aldicarb, manufactured by Union Carbide) |
| S-methyl N-[methylcarbamoyl(oxy)] thioacetamide (lannate) |
| Chlorinated camphene, 67 percent Octachlorocamphene (Toxaphene, manufactured by Hercules) |
| Tricalcium aresenate |
| Sodium aluminum fluoride |
| Dichlorodiphenyltrichloroethane |
| Tricyclohexyltin hydroxide (Plictran, manufactured by Dow Chemical) |

Nematicides

| |
|---|
| O,O-diethyl-O-2,4-dichlorophenyl phosphorothioate(dichlofenthion) |
| O-Ethyl S,S-dipropyl phosphorodithioate (Ethoprop) |

Molluscicides

| | |
|---|---|
| Copper sulfate | Tributyltin fluoride |
| n-tritylmorpholine (trifenmorph) | Sodium pentachlorophenate |

Herbicides

| |
|---|
| 2,4-dichlorophenoxyacetic acid (2,4-D) |
| Alkylamine salts of 2,4-D |
| Butoxyethanol ester of 2,4-D |
| 2,4,5-trichlorophenoxy)propionic acid (Silvex) |
| 3-amino-2,5-dichlorobenzoic acid (chloramben) |
| 3,6-dichloro-O-anisic (Dicamba) |
| 2,3,6-trichlorophenylacetic acid (Fenac) |
| 2,6-dichlorobenzonitrile (Dichlobenil) |
| N,N-diallyl-2-chloroacetamide (Randox) |
| S-Ethyl diisobutylthiocarbamate (Sutan) |
| Isopropyl N-(3-chlorophenyl) carbamate (chloropropham) |
| 3-amino-1,2,4-triazole (Amitrole) |
| 2-chloro-4,6-Bis(ethylamino)-S-triazine (Simazine) |
| 2-chloro-4-ethylamino-6-isopropylamino-S-triazine (Atrazine) |

Fungicides

| |
|---|
| Triphenyltin acetate |
| Methyl-1-(butacarbamoyl)-2-benzimidazole carbamate (Benomyl) |

The self-encapsulating polymeric-containing solution of the present invention is applied by ejecting or spraying a liquid solution or emulsion from known or conventional spray equipment. Such spray equipment can be affixed to any suitable vehicle such as an aircraft, truck, a spray system in a field, and the like, utilizing techniques and artifices common to the particular art, for example, as in the agricultural and public health areas. Subsequently and immediately after ejection, the spray during flight through the intervening atmosphere rapidly loses solvent via evaporation, coacervation occurs, and small solid spheres are formed having generally a very uniformed shape and size. Thus, in-flight encapsulation occurs during the short passage between the egress of a spray or ejection apparatus and a target area with the delivered encapsulated product being a solid. Each sphere or microcapsule is comprised of an outer enveloping polymeric membrane and an inner core of the particle or an agglomeration of particles. The encapsulated product can be delivered to and within the target area using narrow spectrum sprays (for example, that produced by the Beeco Mist Nozzle, designed to provide a sufficient transport of the active ingredient to its target area). Generally, the various spray systems can be adjusted such that a few ounces of the composition or solution is utilized for each acre or up to about 2 to 5 gallons of solution per acre. In the latter case, water is generally utilized as a solvent.

Moreover, applicants' composition, solution and process, aided by the film-forming polymer coating of a particle or particles, can result in fairly uniform-sized encapsulated products, that is, encapsulated products in which at least 90 percent of the products fall within a narrow range, and as set forth hereinabove. Of course, the size of the encapsulated products can be varied by changing the proportion of the various ingredients, the amount of crosslinking agent, and the like, as set forth hereinbelow as well as utilizing different spray equipment, particularly the nozzles thereon which largely determine the initial egress droplet size spectrum. Thus, encapsulated products having a particle size of from 1 micron to 500 microns or larger can be produced. Generally, however, encapsulated products of from about 1 to about 100 microns are desired for many applications. A specific example of a suitable spraying apparatus which delivers droplets over a narrow range is manufactured by the Beeco Products Corporation. As a rough rule of thumb, the encapsulated particle size will be 80 percent of the initial droplet size leaving a spray or ejecting apparatus, when the amount of solvent is equal to the amount of particles on a weight basis. Since great uniformity and droplet size as well as the encapsulated product can be controlled as described herein, the microcapsules of the present invention are ideal as a research tool for the study and evaluation of spray equipment and effects of atmospheric parameters upon the spraying art.

Additionally, micro-encapsulated products of the present invention result in a controlled leaching rate of the particular particle at the site of application or target area so that the particle availability is greatly prolonged and leads to greater efficacy, reduced contamination, and economic benefit. Also, non-persistent agents can be encapsulated and essentially rendered persistent at the microcapsule application site, so that once released in the environment, it becomes subject to natural degradation factors so that persistency is low at the site of application; again a positive contribution to enhance environmental quality.

In addition to varying the components of the generally three-phase system, additional compounds or agents may be added to the solution to control various parameters or functions such as capsule size, the enveloping polymeric membrane thickness, the leaching rate, the rate of evaporation, the emitted droplet size, adhesion, and the like. Naturally, such additives should not have any chemical interaction which any of the components of the system.

Generally, the enveloping polymeric membrane of the polymers of the present invention and, particularly, the preferred interpolymer have relatively little environmental resistance and, thus, the effects of the rain and sun are detrimental to the longevity of the particle. However, longevity can be enhanced in several ways as by increasing the amount or thickness of the enveloping polymer membrane. This can be achieved by utilizing a greater ratio of polymer. Moreover, longevity can be increased by utilizing specific types of polymers such as various specific interpolymers which show improved leaching rates over similar polymers. Crosslinking agents may also be added to the solution so that, upon encapsulation, the polymeric membrane is crosslinked. Crossinking decreases the pore size and, hence, increases duration or longevity so that the final particle may be utilized over a period of several months. Suitable crosslinking agents include the alkaline earth metal salts wherein the alkaline earth is beryllium, magnesium, barium or, preferably, calcium. Suitable anions include carbonate, bicarbonate, nitrate, oxide, hydroxide, and the various halogens, for example, $F^-$, $Cb^-$, $I^-$, and $Br^-$. Of these, the calcium salts, especially calcium hydroxide, are desirable and calcium chloride is preferred. Moreover, the interpolymers may be crosslinked with zinc oxide as taught in U.S. Pat. No. 3,749,772. Generally, the extent of the crosslinking agent may range from about 0.01 to about 0.5 percent by weight based upon the total weight of the solution with the range of from about 0.05 to about0.25 being preferred. Naturally, the crosslinking agents should be non-toxic, generally, non-reactive with the components, and soluble in the solvents of the present invention.

The self-encapsulating polymeric-containing solution of the present invention, generally, must be maintained in relatively a non-acidic state, usually at a pH of 6.5 to 8.0, to prevent crosslinking prior to solvent evaporation. Typical alkaline agents may be utilized to achieve such a pH range, such as ammonia, sodium hydroxide, and the like. Normally, only very small amounts are required as on the range of 0.01 to about 1.0 percent by weight of the total solution.

In many applications, especially those involving the delivery of insecticides to protect crops and the like, long term adhesion of the microcapsule to foliage or other plant structures is desired. Improved adhesion can be obtained by generally utilizing the lower molecular weight interpolymers and/or adhesive agents such as small amounts of alkyl esters as from 0.01 to 3 percent by weight based upon the total solution. The alkyl esters are of the formula

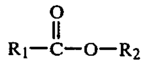

where $R_1$ and $R_2$ contain from 2 to 5 carbon atoms with Ethyl acetate being preferred.

The effect of the various ingredients upon the membrane thickness, adhesion, longevity of release and the like will be better understood by reference to Table I which sets forth formulations in Examples 1 through 12. In Example 1, the interpolymer utilized was 16 percent of a high molecular type such as Carboset 525, 50 percent by weight of alcohol, and 34 percent by weight of the particle. In Example 1, the particle was actually in solution as a 50-50 mixture of benzoic acid and orthotoluic acid. This example, as well as the other examples were sprayed through a Beeco Mist spray gun utilizing a 60-micron pore size nozzle. The polymeric film totally encapsulated the crystallized acids used as a particle and the encapsulated product were spheres. Example 2 illustrates a crosslinked version of Example 1 wherein calcium chloride was used as a crosslinking agent along with a small amount of ammonia to prevent premature crosslinking prior to solvent evaporation. The thickness of the polymer membrane was greater than that of Example 1. Decreasing the average molecular weight of the polymer component as in Example 3 decreases the membrane or wall thickness and, thus, lowers the field life of the capsule. For long life, that is from about 3 to 6 months, the polymer of Example 4 may be crosslinked as shown in Example 5.

As previously noted, the use of low molecular weight polymers provide some degree of tackiness so that the encapsulated product will adhere to leaves, stems, and the like. However, since lower molecular weight polymers are often deleterious to film-forming properties, increased adhesion time of several weeks and even several months can be obtained by adding small amounts of ethyl acetate or butyl cellosolve, as set forth in the formulation of Example 6. The process of adhesion promotion is as follows. Utilizing the formulation of Example 7, the microcapsule forms and crosslinking occurs, as soon as the alcohol and ammonia evaporate, the process being essentially complete in a few seconds after the egress from a spraying apparatus and also depending upon the droplet surface area. However, the ethyl acetate or butyl cellosolve is occluded by the forming envelope and, thus, for the most part, is present at the time of foliage contact. At the instant of such contact and for several seconds thereafter, the ethyl acetate moves from the microcapsule, penetrating the outermost dermis of the plant. This process, mainly a desorption phenomenon, results in a slight flow of the polymer envelope into the foliage structure, thus enhancing adhesion. The process is rapid and relies on a very minute quality of an adhesive aid, such as ethyl acetate. Moreover, no damage to agricultural important plants arises from momentary contact with the ethyl acetate.

Water systems and water/alcohol systems have also been utilized as where the uses of a diluted alcohol would be advantageous. Examples 8 and 9 illustrate such systems, based upon a water soluble interpolymer, particularly, Carboset XLII. In Example 8, a pure water system is utilized and, hence, the particles are limited to water soluble compounds. Although this formulation is of poor environmental resistance, it is used in delivering trace nutrients such as water soluble zinc, copper, iron, and other salts. The formulations of Examples 8 and 9 result in capsule formation during flight, but due to the amount of $H_2O$ present at the time of impact, the effects may be a soft capsule that flows to meet the contour of the impingement surface. Rigid spheres are usually not formed. Such systems may also be crosslinked and adhesion promoted. In contrast, the porosity of a microcapsule may be enhanced by the utilization of an alcohol insoluble with a water soluble additive such as calcium benzoate, calcium hydroxide, and calcium carbonate. Considering Example 10, during in-flight encapsulation, most of the calcium chloride is trapped within a polymer membrane. However, once the crosslinked capsule has adhered to a given surface and comes into contact with water, the porosigon, calcium benzoate, is rapidly lost through leaching and a pore structure remains allowing water penetration of the core particle. When calcium hydroxide is used as in Example 11, it not only serves to crosslink the polymer but also imparts alkalinity and, thus, no ammonia is necessary. Since calcium hydroxide is alcohol soluble, a considerable fraction is found in the core area. However, sufficient quantities exist within the polymer envelope to enhance the growth of porosity.

TABLE I

| | RECIPE | | | | | | | | | | | |
|---|---|---|---|---|---|---|---|---|---|---|---|---|
| | EXAMPLE | | | | | | | | | | | |
| INGREDIENT | 1 | 2 | 3 | 4 | 5 | 6 | 7 | 8 | 9 | 10 | 11 | 12 |
| Carboset 525 | 16% | 16% | 8% | 6% | 6% | 6% | 6% | — | — | 12% | 11% | 12% |
| Carboset 526 | — | — | — | 7% | 7% | — | — | — | — | — | — | — |
| Carboset XL11 | — | — | 8% | — | — | — | — | 4% | 6.25 | 12% | 12% | 10% |
| Carboset 514 | — | — | — | — | — | 6% | 6% | — | — | — | — | — |
| Ethanol | 50% | 50% | 50% | 69% | 69% | 66% | 66% | — | — | 37.85 | 27% | 44% |
| Water | — | — | — | — | — | — | — | 89.75% | 87.5% | 7% | 15% | — |
| Ethyl Acetate | — | — | — | — | — | 1% | 1% | — | — | — | — | — |
| Calcium Chloride | — | 0.1% | — | — | 0.2% | — | 0.2% | — | — | 0.1% | — | — |
| Ammonia | — | 0.05% | — | — | 0.1% | — | 0.1% | — | — | 0.05% | — | — |
| Calcium Benzoate | — | — | — | — | — | — | — | — | — | 1% | — | — |
| Calcium Hydroxide | — | — | — | — | — | — | — | — | — | — | 2% | — |
| Lauric Acid | — | — | — | — | — | — | — | — | — | — | — | 3% |
| Agent | 34% | 33.85% | 33% | 18% | 17.7% | 21% | 20.7% | 6.25% | 6.25% | 30% | 32% | 31% |

The invention will be better understood by reference to the following additional examples.

EXAMPLE A

Figure 2:
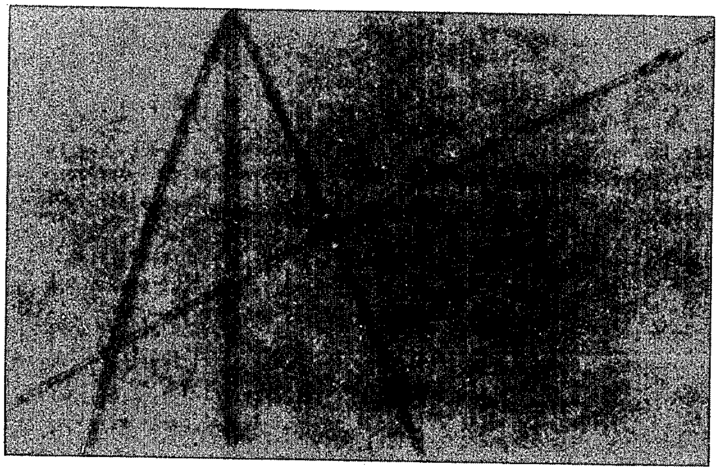
FIG. 2 is a photograph similar to FIG.1 wherein the encapsulated particle is adhered to the junction of two glass strands.
Figure 3:
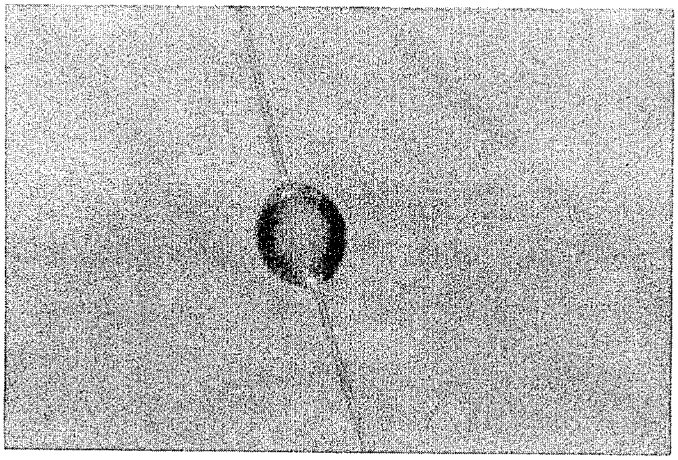
FIG. 3 is another photograph showing a particle polymerically encapsulated about a glass strand.
Figure 4:
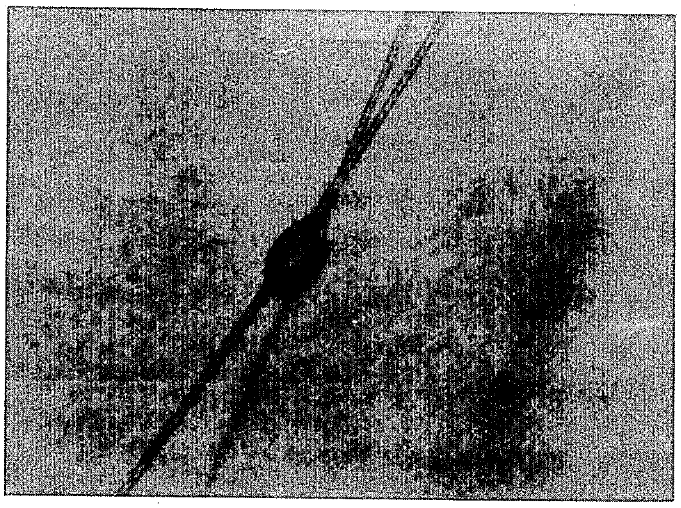
FIG. 4 is another photograph showing an encapsulated particle attached to the intersection of two glass strands.

A solution containing 75 parts by weight of pyrethrin-piperonyl butoxide, 25 parts by weight of Carboset 525, and 100 parts by weight of ethanol was made. The solution was mixed and added to a manual spray ejector such as a hand-operated atomizing pump. The solution was sprayed in the direction of glass fibers located approximately 1 to 2 feet away from the egress of the spray pump. Upon spraying, the Carboset encapsulated the pyrethrin-piperonyl butoxide. The graphic analysis, as shown in photographs 1 through 4, clearly depicts the polymeric film formed about the pyrethrin-piperonyl butoxide particle. The glass strands in all photographs are 10 microns in diameter. As apparent from the photographs, FIG. 1 definitely shows a polymer formed about the particle, with the polymer adhered to a glass strand. In FIG. 2, the polymer is formed about the intersection of two strands with another encapsulated particle located about a single strand. FIG. 3 discloses the encapsulated film being located about the liquid particle. In this photograph, the film actually formed completely about a portion of the glass strand. FIG. 4 is similar to FIG. 2 in that it reveals a polymeric film formed about the intersection of two glass strands with a liquid particle being located therein.

EXAMPLE B

Thirty parts by weight of Carboset XL11 having a molecular weight of approximately 45,000 and a 30 percent aqueous dispersion was mixed with 100 parts of water. To this was added 120 parts of Dursban containing 75 percent of an active ingredient of O,O-diethyl-O-3,5,6-trichloropyridinylthrionophosphate. These ingredients were mixed and the solution had a pH of 6.7. Utilizing a hand spray pump, the solution was sprayed towards a target area. Photographs reveal that the active ingredient was fully encapsulated by the particle.

While having described the invention in accordance with the patent statutes, the invention is measured by the following claims.

What is claimed is:

1. An encapsulated particle having been in situ encapsulated and concurrently and directly adhered to an earth target, comprising:

a particle, said particle encapsulated with a polymer, said polymer selected from the class consisting of (a) polyvinyl acetate; (b) a polyvinyl ether wherein said repeating unit has from 2 to 10 carbon atoms; (c) an acrylic polymer or a copolymer made from monomers having the formula

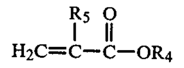

where $R_4$ is hydrogen or an alkyl, cycloalkyl, aryl, or aralkyl having from 1 to 30 carbon atoms and $R_5$ is hydrogen or an alkyl, cycloalkyl, aryl, or aralkyl having from 1 to 12 carbon atoms; (d) the salt of (1) an interpolymer having the structure

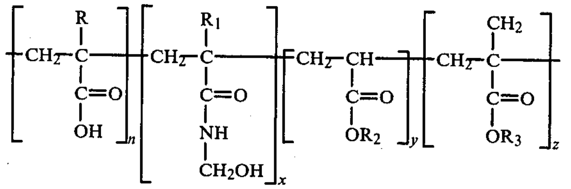

wherein R and $R_1$ are members of the group consisting of hydrogen and methyl; $R_2$ is a member of the group consisting of methyl, ethyl, propyl and butyl; $R_3$ is a member of the group consisting of methyl and ethyl; n represents from 3 to 12 weight percent based on the combined weight of n, x, y and z; x represents from 8 to 25 percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of n+x+y+z is always exactly 100 and the groups n, x, y and z are present in a heterogeneous relative position, and (2) a member of the group consisting of ammonia, hydrazine, a low boiling primary aliphatic amine and a low boiling secondary aliphatic amine, said salt being soluble in water in the pH range of from about 5 to 8; and (e) combinations thereof; and said particle having been in situ encapsulated and concurrently and directly applied to the earth target;

said encapsulated particle containing a small amount of an adhesive agent so that said encapsulated particle has improved tackiness and adheres to said earth target.

2. An encapsulated particle according to claim 1, wherein the molecular weight of said polyvinyl acetate ranges from about 10,000 to about 100,000, wherein the molecular weight of said polyvinyl ether ranges from about 10,000 to about 100,000, wherein the molecular weight of said acrylic polymers ranges from about 10,000 to about 600,000, and wherein the molecular weight of said interpolymer ranges from about 20,000 to about 1,000,000.

3. An encapsulated particle according to claim 2, including adding crosslinking agents for reaction with said polymer upon ejection, and including an alkaline compound so that the pH of said solution ranges from about 6.5 to about 8.0, said crosslinking agent being an alkaline earth salt, said alkaline earth salt selected from the group consisting of calcium, barium, beryllium and magnesium, said anion portion of said salt selected from the group consisting of carbonate, bicarbonate, oxide, hydroxide, nitrate, $F^-$, $Cl^-$, $I^-$ and $Br^-$, the amount of said crosslinking agent ranging from about 0.01 to about 5 percent by weight based upon the total weight of said solution and the amount of said alkaline compound ranging from about 0.01 to about 1 percent by weight based upon the total weight of said solution.

4. An encapsulated particle according to claim 2, wherein said adhesive agent has the formula

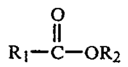

wherein $R_1$ and $R_2$ have from 2 to 5 carbon atoms, and the amount of said adhesive agent ranges from about 0.01 to about 3 percent by weight based upon the total weight of said solution.

5. An encapsulated particle according to claim 2, wherein said particle is selected from the group consisting of insecticides, fungicides, herbicides, nutrients, trace minerals, nematicides, molluscicides, acaricides, pheromones, odorants, attractants, fragrances, and repellants.

6. An encapsulated particle according to claim 5, wherein said trace mineral is selected from the group consisting of zinc chloride, zinc sulfate, ferric chloride, ferric sulfate, copper sulfate, copper oxychloride, boric acid, sodium borate, sodium selenate, cobalt sulfate, sodium molybdate, manganese chloride, and combinations thereof;

wherein said insecticides and said acaricides are selected from the group consisting of pyrethrin-piperonyl butoxide, O,O-dimethyl-O-p-nitrophenyl phosphorothioate, O,O-dimethyl-O-(3-methyl-4-nitrophenyl)phosphorothioate, O,O-diethyl-O-(2-isopropyl-6-methyl-5-pyrimidinyl) phosphorothioate, O,O-dimethyl-O-[3-methyl-4-(methylthio)-phenyl]phosphorothioate, 1-naphthyl methyl-carbamate, 2-(1-methylethoxy)phenol methylcarbamate, 2-methyl-2-(methylthio)propionaldehyde-O-(methyl carbamoyl)oxime, S-methyl-N-[methyl carbamoyl (oxy)]thioacetamide, chlorinated camphene, 67 percent octachlorocamphene, tricalcium aresenate, sodium aluminum fluoride, dichlorodiphenyltrichloroethane, tricyclohexyltin hydroxide, and combinations thereof;

wherein said nematicides include O,O-diethyl-O-2,4-dichlorophenyl phosphorothioate, O-ethyl S,S-dipropyl phosphorodithioate, and combinations thereof;

wherein said mulluscicides include copper sulfate, tributyltin fluoride, n-tritylmorpholine, sodium pentachlorophenate, and combinations thereof;

wherein said herbicides include 2,4-dichlorophenoxyacetic acid, alkylamine salts of 2,4-D, butoxyethanol ester of 2,4-D, 2,4,5-trichlorophenoxyacetic acid, 2-(2,4,5-trichlorophenoxy)propionic acid, 3-amino-2,5-dichlorobenzoic acid, 3,6-dichloro-O-anisic acid, 2,3,6-trichlorophenylacetic acid, 2,6-dichlorobenzonitrile, N,N-diallyl-2-chloroacetamide, isopropyl N-(3-chlorophenyl) carbamate, S-ethyl diisobutylthiocarbamate, 3-amino-1,2,4-triazole, 2-chloro-4,6-Bis(ethylamino)-S-triazine, 2-chloro-4-ethylamino-6-isopropylamino-S-triazine, and combinations thereof; and wherein said fungicides include triphenyltin acetate, methyl-1-(butacarbamoyl)-2-benzimidazole carbamate, and combinations thereof.

7. An encapsulated particle according to claim 5, wherein the amount of said polymer ranges from about 0.3 to about 25 parts by weight, and wherein the amount of said particle ranges from about 1 to about 40 parts by weight.

8. An encapsulated particle according to claim 7, including an adhesive agent, said adhesive agent being an alkyl ester of the formula

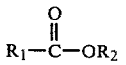

wherein $R_1$ and $R_2$ have from 2 to 5 carbon atoms, and the amount of said adhesive agent ranges from about 0.01 to about 3 parts by weight based upon the total weight of said encapsulated particle.

9. An encapsulated particle according to claims 5, 6, 7, or 8, wherein said polymer is said polyvinyl acetate.

10. An encapsulated particle according to claims 5, 6, 7, or 8, wherein said polymer is said polyvinyl ether.

11. An encapsulated particle according to claim 10, wherein said polyvinyl ether has two carbon atoms in the repeating unit.

12. An encapsulated particle according to claims 5, 6, 7, or 8, wherein said polymer is said acrylic polymer or copolymer.

13. An encapsulated particle according to claim 12, wherein $R_4$ of said formulation is hydrogen or an alkyl having from 1 to 4 carbon atoms, and wherein said $R_5$ of said formula is hydrogen or an alkyl having from 1 to 3 carbon atoms, and wherein the molecular weight of said polymer or said copolymer ranges from about 30,000 to about 300,000.

14. An encapsulated particle according to claims 5, 6, 7, or 8, wherein said polymer is said interpolymer.

15. A process for the in situ encapsulation of particles between a spraying apparatus and an earth target, comprising the steps of:

preparing a self-encapsulating polymeric-containing solution;

said solution comprising by weight from about 0.3 percent to about 25 percent of a polymer, from about 35 percent to about 99 percent of a solvent, said solvent being a compound which will solubilize said polymer, and from about 1 percent to about 40 percent of the particles, said particle being soluble or dispersible in said solvent;

said polymer selected from the class consisting of (a) polyvinyl acetate; (b) a polyvinyl ether within said repeating unit has from 2 to 10 carbon atoms; (c) an acrylic polymer or a copolymer made from monomers having the formula

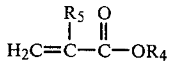

wherein $R_4$ is hydrogen or an alkyl, cycloalkyl, aryl, or aralkyl having from 1 to 30 carbon atoms and $R_5$ is hydrogen or an alkyl, cycloalkyl, aryl, or aralkyl having from 1 to 12 carbon atoms; (d) the salt of (1) an interpolymer having the structure

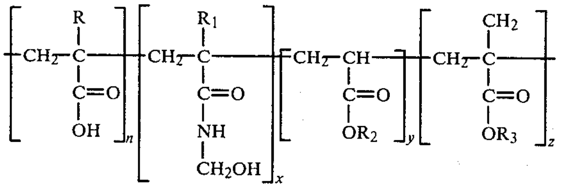

wherein R and $R_1$ are members of the group consisting of hydrogen and methyl; $R_2$ is a member of the group consisting of methyl, ethyl, propyl and butyl; $R_3$ is a member of the group consisting of methyl and ethyl; n represents from 3 to 12 weight percent based on the combined weight of n, x, y and z; x represents from 8 to 25 percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of $n+x+y+z$ is always exactly 100 and the groups n, x, y and z are present in a heterogeneous relative position, and (2) a member of the group consisting of ammonia, hydrazine, a low boiling primary aliphatic amine and a low boiling secondary aliphatic amine, said salt being soluble in water in the pH range of from about 5 to 8; and (e) combinations thereof;

in situ encapsulating said soluble or dispersible particle by:

spraying into the earth's atmosphere said solution containing said soluble or dispersible particle from a spray apparatus, and immediately thereafter;

evaporating said solvent in aid earth's atmosphere, and coacervating during the passage from said spraying apparatus to an earth target said polymer and said particle in said earth's atmosphere so that said polymer substantially encapsulates said particle, and concurrently and directly applying said encapsulated particle to an earth target.

16. A process according to claim 15, wherein the molecular weight of said polyvinyl acetate ranges from about 10,000 to about 100,000, wherein the molecular weight of said polyvinyl ether ranges from about 10,000 to about 100,000, wherein the molecular weight of said acrylic polymer or copolymer ranges from about 10,000 to about 60,000, and wherein the molecular weight of said interpolymer ranges from about 20,000 to about 1,000,000.

17. A process according to claim 16, wherein said solvent is selected from the group consisting of alcohols having from 1 to 5 carbon atoms, acetone, diisobutyl ketone, methyl ethyl ketone, dioxane, methylene chloride, water, and combinations thereof.

18. A process according to claim 16, wherein said particle is selected from the group consisting of an insecticide, a trace mineral, an acaricide, a nematicide, a molluscicide, a herbicide, a fungicide, a pheromone, an odorant, a fragrance, an attractant, a repellant, and combinations thereof.

19. A process according to claim 18, wherein said solvent is selected from the group consisting of alcohols having from 1 to 5 carbon atoms, acetone, diisobutyl ketone, methyl ethyl ketone, dioxane, methylene chloride, water, and combinations thereof.

20. A process according to claim 19, including adding crosslinking agents to said solution prior to ejection for reaction with said polymer, and including the step of adding an alkaline compound to said solution so that the pH of said solution ranges from about 6.5 to about 8.0, said crosslinking agent being an alkaline earth salt, said alkaline earth salt selected from the group consisting of calcium, barium, beryllium and magnesium, said anion portion of said salt selected from the group consisting of carbonate, bicarbonate, oxide, hydroxide, nitrate, $F^-$, $Cl^-$, $I^-$ and $Br^-$, the amount of said crosslinking agent ranging from about 0.01 to about 5 percent by weight based upon the total weight of said solution and the amount of said alkaline compound ranging from about 0.01 to about 1 percent by weight based upon the total weight of said solution.

21. A process according to claim 19, including adding an adhesive agent so that upon the in situ formation of an encapsulated particle from said solution and the concurrent and direct application of said encapsulated particle to an inert target, said adhesive agent improves the tackiness of said encapsulated particle to said target.

22. A process according to claim 21, wherein said adhesive agent is an alkyl ester having the formula

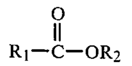

wherein $R_1$ and $R_2$ have from 2 to 5 carbon atoms, and the amount of said adhesive agent ranges from about 0.01 to about 3 percent by weight based upon the total weight of said solution.

23. A process according to claim 18, wherein said trace mineral is selected from the group consisting of zinc chloride, zinc sulfate, ferric chloride, ferric sulfate, copper sulfate, copper oxychloride, boric acid, sodium borate, sodium selenate, cobalt sulfate, sodium molybdate, manganese chloride, and combinations thereof, wherein said Nematicide is selected from the group consisting of O,O-dietyl-0-2,4-dichlorophenyl phosphorodithioate, O-ethyl-S,S-dipropyl phosphorodithioate (Ethoprop), and combinations thereof, wherein said molluscicide is selected from the group consisting of copper sulfate, n-tritylmorpholine (trifenmorph), tributyltin fluoride, sodium pentachlorphenate, and combinations thereof, and wherein said fungicide is selected from the group consisting of triphenyltin acetate, methyl-1-(butacarbamoyl)-2-benzimidazole carbamate (Benomyl), and combinations thereof.

24. A process according to claim 23, wherein said solvent is selected from the group consisting of alcohols having from 1 to 5 carbon atoms, acetone, diisobutyl ketone, methyl ethyl ketone, dioxane, methylene chloride, water, and combinations thereof.

25. A process according to claim 24, including adding crosslinking agents to said solution prior to ejection for reaction with said polymer, and including the step of adding an alkaline compound to said solution so that the pH of said solution ranges from about 6.5 to about 8.0, said crosslinking agent being an alkaline earth salt, said alkaline earth salt selected from the group consisting of calcium, barium, beryllium and magnesium, said anion portion of said salt selected from the group consisting of carbonate, bicarbonate, oxide, hydroxide, nitrate, $F^-$, $Cl^-$, $I^-$ and $Br^-$, the amount of said crosslinking agent ranging from about 0.01 to about 5 percent by weight based upon the total weight of said solution and the amount of said alkaline compound ranging from about 0.01 to about 1 percent by weight based upon the total weight of said solution.

26. A process according to claim 24, including adding an adhesive agnet so that upon the in situ formation of an encapsulated particle from said solution and the concurrent and direct application of said encapsulated particle to an inert target, said adhesive agent improves the tackiness of said encapsulated particle to said target.

27. A process according to claim 26, wherein said adhesive agent is an alkyl ester having the formula $$R_1-\overset{\overset{O}{\|}}{C}-OR_2$$

wherein $R_1$ and $R_2$ have from 2 to 5 carbon atoms, and the amount of said adhesive agent ranges from about 0.01 to about 3 percent by weight based upon the total weight of said solution.

28. A process according to claim 27, wherein said solvent is selected from the group consisting of water, alcohols having from 1 to 5 carbon atoms, and combinations thereof.

29. A process according to claim 18, wherein said particle is a herbicide, said herbicide selected from the group consisting of 2,4-dichlorophenoxyacetic acid (2,4-D), alkylamine salts of 2,4-D, butyoxyethanol ester of 2,4-D, 2,4,5-trichlorophenoxyacetic acid (2,4,5-T), 2-(2,4,5-trichlorophenoxy)propionic acid (Silvex), 3-amino-2,5-dichlorobenzoic acid (chloramben), 3,6-dichloro-O-anisic acid (Dicamba), 2,3,5-trichlorophenylacetic acid (Fenac), 2,6-dichlorobenzonitrile (Dichlobenil), N,N-diallyl-2-chloroacetamine (Randox), S-ethyl diisobutylthiocarbamate (Sutan), isopropyl N-(3-chlorophenyl) carbamate (chloropropham), 3-amino-1,2,4-triazole (Amitrole), 2-chloro-4,6-Bis (ethylamino)-isopropylamino-S-triazine (Atrazine), and combinations thereof.

30. A process according to claim 29, wherein said solvent is selected from the group consisting of alcohols having from 1 to 5 carbon atoms, acetone, diisobutyl ketone, methyl ethyl ketone, dioxane, methylene chloride, water, and combinations thereof.

31. A process according to claim 30, including adding crosslinking agents to said solution prior to ejection for reaction with said polymer, and including the step of adding an alkaline compound to said solution so that the pH of said solution ranges from about 6.5 to about 8.0, said crosslinking agent being an alkaline earth salt, said alkaline earth salt selected from the group consisting of calcium, barium, beryllium and magnesium, said anion portion of said salt selected from the group consisting of carbonate, bicarbonate, oxide, hydroxide, nitrate, $F^-$, $Cl^-$, $I^-$, $Br^-$, the amount of said crosslinking agent ranging from about 0.01 to about 5 percent by weight based upon the total weight of said solution and the amount of said alkaline compound ranging from about 0.01 to about 1 percent by weight based upon the total weight of said solution.

32. A process according to claim 29, including adding an adhesive agent so that upon the in situ formation of an encapsulated particle from said solution and the concurrent and direct application of said encapsulated particle to an inert target, said adhesive agent improves the tackiness of said encapsulated particle to said target.

33. A process according to claim 32, wherein said adhesive agent is an alkyl ester having the formula $$R_1-\overset{\overset{O}{\|}}{C}-OR_2$$

wherein $R_1$ and $R_2$ have from 2 to 5 carbon atoms, and the amount of said adhesive agent ranges from about 0.01 to about 3 percent by weight based upon the total weight of said solution.

34. A process according to claim 33, wherein said solvent is selected from the group consisting of water, alcohols having from 1 to 5 carbon atoms, and combinations thereof.

35. A process according to claim 18, wherein said particle is a pheromone.

36. A process according to claim 19, wherein said particle is a pheromone.

37. A process according to claim 21, wherein said particle is a pheromone.

38. A process according to claim 22, wherein said particle is a pheromone.

39. A process according to claim 18, wherein said particle is an insecticide or an acaricide selected from the group consisting of O,O-diethyl-O-p-nitrophenyl phosphorothioate (Parathion), O,O-dimethyl-O-p-nitrophenyl phosphorothioate (Methyl parathion), O,O-dimethyl-O-(3-methyl-4-nitrophenyl)phosphorothioate (Sumithion), O,O-diethyl-O-(2-isopropyl-6-methyl-5-pyrimidinyl)phosphorothioate (Diazinon), O,O-dimethyl-O-[3-methyl-4-(methylthio)phenyl]phosphorothioate (Fenthion), Pyrethrin-piperonyl butoxide, 1-naphthyl methylcarbamate (Carbaryl), 2-(1-methylethoxy)phenyl methylcarbamate (Baygon), 2-methyl-2-(methylthio)-propionaldehyde-O-(methyl carbamonyl) oxime (Aldicarb), S-methyl N-[methylcarbamonyl(oxy)]thioacetamine (lannate), chlorinated camphene, 67 percent octachlorocamphene (Toxaphene), tricalcium aresenate, sodium aluminun fluoride, Dichlorodiphenyltrichloroethane, tricyclohexyltin hydroxide (Plictran), and combinations thereof.

40. A process according to claim 39, wherein said solvent is selected from the group consisting of alcohols having from 1 to 5 carbon atoms, acetone, diisobutyl ketone, methyl ethyl ketone, dioxane, methylene chloride, water, and combinations thereof.

41. A process according to claim 40, including adding crosslinking agents to said solution prior to ejection for reaction with said polymer, and including the step of adding an alkaline compound to said solution so that the pH of said solution ranges from about 6.5 to about 8.0, said crosslinking agent being an alkaline earth salt, said alkaline earth salt selected from the group consisting of calcium, barium, beryllium and magnesium, said anion portion of said salt selected from the group consisting of carbonate, bicarbonate, oxide, hydroxide, nitrate, $F^-$, $Cl^-$, $I^-$ and $Br^-$, the amount of said crosslinking agent ranging from about 0.01 to about 5 percent by weight based upon the total weight of said solution and the amount of said alkaline compound ranging from about 0.01 to about 1 percent by weight based upon the total weight of said solution.

42. A process according to claim 40, including adding an adhesive agent so that upon the in situ formation of an encapsulated particle from said solution and the concurrent and direct application of said encapsulated particle to an inert target, said adhesive agent improves the tackiness of said encapsulated particle to said target.

43. A process according to claim 42, wherein said adhesive agent is an alkyl ester having the formula

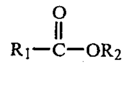

wherein $R_1$ and $R_2$ have from 2 to 5 carbon atoms, and the amount of said adhesive agent ranges from about 0.01 to about 3 percent by weight based upon the total weight of said solution.

44. A process according to claim 43, wherein said solvent is selected from the group consisting of water, alcohols having from 1 to 5 carbon atoms, and combinations thereof.

45. A process according to claim 23, 26, 28, 29, 32, 34, 35, 38, 39, 42, or 44, wherein said polymer is said polyvinyl acetate.

46. A process according to claim 23, 26, 28, 29, 32, 34, 35, 38, 39, 42, or 44, wherein said polymer is said polyvinyl ether.

47. A process according to claim 46, wherein said polyvinyl ether has two carbon atoms in the repeating group.

48. A process according to claim 23, 26, 28, 29, 32, 34, 35, 38, 39, 42, or 44, wherein said polymer is said acrylic polymer or copolymer.

49. A process according to claim 48, wherein $R_4$ of said formulation is hydrogen or a alkyl having from 1 to 4 carbon atoms, and wherein said $R_5$ of said formula is hydrogen or an alkyl having from 1 to 3 carbon atoms, and wherein the molecular weight of said polymer of said copolymer ranges from about 30,000 to about 300,000.

50. A process according to claim 23, 26, 28, 29, 32, 34, 35, 38, 39, 42, or 44, wherein said polymer is said interpolymer salt.

51. A process according to claim 50, wherein in said interpolymer salt, n is 4, x is 10, y is 86, and z is 0.

52. A process according to claim 50, wherein in said interpolymer salt, n is 8, x is 17, y ix 52.5 and z is 22.5.

53. A process according to claim 50, wherein in said interpolymer salt, n is 8, x is 17, y is 75, and z is 0.

54. A process according to claim 23, 26, 28, 29, 32, 34, 35, 38, 39, 42, or 44, wherein the amount of said polymer ranges from about 4 percent to about 13 percent by weight, wherein the amount of said solvent ranges from about 50 percent to about 90 percent by weight, and wherein the amount of said particle ranges from about 5 percent to about 30 percent by weight.

55. A process according to claim 45, wherein the amount of said polymer ranges from about 4 percent to about 13 percent by weight, wherein the amount of said solvent ranges from about 50 percent to about 90 percent by weight, and wherein the amount of said particle ranges from about 5 percent to about 30 percent by weight.

56. A process according to claim 46, wherein the amount of said polymer ranges from about 4 percent to about 13 percent by weight, wherein the amount of said solvent ranges from about 50 percent to about 90 percent by weight, and wherein the amount of said particle ranges from about 5 percent to about 30 percent by weight.

57. A process according to claim 48, wherein the amount of said polymer ranges from about 4 percent to about 13 percent by weight, wherein the amount of said solvent ranges from about 50 percent to about 90 percent by weight, and wherein the amount of said particle ranges from about 5 percent to about 30 percent by weight.

58. A process according to claim 50, wherein the amount of said polymer ranges from about 4 percent to about 13 percent by weight, wherein the amount of said solvent ranges from about 50 percent to about 90 percent by weight, and wherein the amount of said particle ranges from about 5 percent to about 30 percent by weight.

59. A process according to claim 50, wherein in said interpolymer salt, n is 8, x is 17, y ix 37.5, and z is 37.5.

60. An in situ self-encapsulating polymericcontaining solution for concurrent and direct application to an earth target, comprising by weight, based upon the total weight of said solution from about 0.3 percent to about 25 percent of a polymer, from about 35 percent to about 99 percent of a solvent, and from about 1 percent to about 40 percent of a particle, said polymer selected from the group consisting of (a) a polyvinyl acetate, (b) a polyvinyl ether wherein said repeating unit has from 3 to 10 carbon atoms, (c) an acrylic polymer or a copolymer made from monomers having the formula

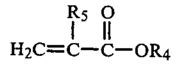

where $R_4$ is hydrogen or an alkyl, cycloalkyl, aryl, or aralkyl having from 1 to 30 carbon atoms and $R_5$ is hydrogen or an alkyl, cycloalkyl, aryl, or aralkyl having from 1 to 12 carbon atoms; (d) the salt of (1) an interpolymer having the structure

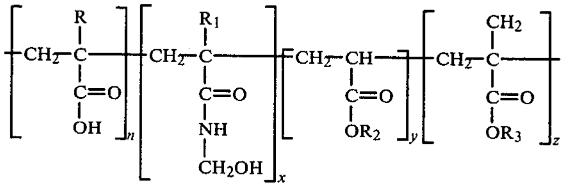

wherein R and $R_1$ are members of the group consisting of hydrogen and methyl; $R_2$ is a member of the group consisting of methyl, ethyl, propyl and butyl; $R_3$ is a member of the group consisting of methyl and ethyl; n represents from 3 to 12 weight percent based on the combined weight of n, x, y and z; x represents from 8 to 25 percent based on the combined weight of n, x, y and z; y represents from 45 to 89 weight percent based on the combined weight of n, x, y and z; z represents from 0 to 44 weight percent based on the combined weight of n, x, y and z; the sum of the numerical value of n+x+y+z is always exactly 100 and the groups n, x, y and z are present in a heterogeneous relative position, and (2) a member of the group consisting of ammonia, hydrazine, a low boiling primary aliphatic amine and a low boiling secondary aliphatic amine, said salt being soluble in water in the pH range of from about 5 to 8; and (e) combinations thereof;

said particle being soluble or dispersible in said solvent;

said solvent being a compound in which said polymer is soluble; and a small amount of weight based upon the total weight of the solution of an adhesive agent so that upon the in situ formation of an encapsulated particle from said solution and the concurrent and direct application of said encapsulated particle to an earth target, said adhesive agent improves the tackiness of said encapsulated particle to said target.

61. A solution according to claim 60, wherein the molecular weight of said polyvinyl acetate ranges from about 10,000 to about 100,000, wherein the molecular weight of said polyvinyl ether ranges from about 10,000 to about 100,000, wherein the molecular weight of said acrylic polymer or copolymer ranges from about 10,000 to about 600,000, and wherein the molecular weight of said interpolymer ranges from about 20,000 to about 1,000,000.

62. A solution according to claim 61, wherein said solvent is selected from the group consisting of alcohols having from 1 to 5 carbon atoms, acetone, diisobutyl ketone, methyl ethyl ketone, dioxane, methylene chloride, water, and combinations thereof.

63. A solution according to claim 62, including crosslinking agents for reaction with said polymer upon ejection and including an alkaline compound so that the pH of said solution ranges from about 6.5 to about 8.0, said crosslinking agent being an alkaline earth salt, said alkaline earth salt selected from the group consisting of calcium, barium, beryllium and magnesium, said anion portion of said salt selected from the group consisting of carbonate, bicarbonate, oxide, hydroxide, nitrate, $F^-$, $Cl^-$, $I^-$, $Br^-$, the amount of said crosslinking agent ranging from about 0.01 to about 5 percent by weight based upon the total weight of said solution and the amount of said alkaline compound ranging from about 0.01 to about 1 percent by weight based upon the total weight of said solution.

64. A solution according to claim 62, wherein said adhesive agent has the formula

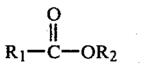

wherein $R_1$ and $R_2$ have from 2 to 5 carbon atoms, and the amount of said adhesive agent ranges from about 0.01 to about 3 percent by weight based upon the total weight of said solution.

65. A solution according to claim 61, wherein said particle is selected from the group consisting of an insecticide, a trace mineral, an acaricide, a nematicide, a molluscicide, a herbicide, a fungicide, a pheromone, an odorant, a fragrance, an attractant, a repellant, and combinations thereof.

66. A solution according to claim 65, wherein said solvent is selected from the group consisting of alcohols having from 1 to 5 carbon atoms, acetone, diisobutyl ketone, methyl ethyl ketone, dioxane, methylene chloride, water, and combinations thereof.

67. A solution according to claim 66, wherein the amount of said polymer ranges from about 4 percent to about 13 percent by weight, wherein the amount of said solvent ranges from about 50 percent to about 90 percent by weight, and wherein the amount of said particle ranges from about 5 percent to about 30 percent by weight.

68. A solution according to claim 67, wherein said adhesive agent has the formula

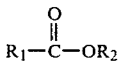

wherein $R_1$ and $R_2$ have from 2 to 5 carbon atoms, and the amount of said adhesive agent ranges from about 0.01 to about 3 percent by weight based upon the total weight of said solution.

69. A solution according to claim 68, wherein said solvent is selected from the group consisting of water, an alcohol having from 1 to 5 carbon atoms, and combinations thereof.

70. A solution according to claim 65, wherein said trace mineral is selected from the group consisting of zinc chloride, zinc sulfate, ferric chloride, ferric sulfate, copper sulfate, copper oxychloride, boric acid, sodium borate, sodium selenate, cobalt surface, sodium molybdate, manganese chloride, and combinations thereof; wherein said insecticide and said acaricide is selected from the group consisting of O,O-diethyl-O-p-nitrophenyl phosphorothioate (Parathion), O,O-dimethyl-O-p-nitrophenyl phosphorothioate (Methyl parathion), O,O-dimethyl-O-(3-methyl-4-nitrophenyl)phosphorothioate (Sumithion), O,O-diethyl-O-(2-isopropyl-6-methyl-5-pyrimidinyl)phosphorothioate (Diazinon), O,O-dimethyl-O-[3-methyl-4-(methylthio)phenyl]phosphorothioate (Fenthion), Pyrethrin-piperonyl butoxide, 1-naphthyl methylcarbamate (Carbaryl), 2-(1-methylethoxy)phenyl methylcarbamate (Baygon), 2-methyl-2-(methylthio) propionaldehyde-O-(methyl carbamonyl) oxime (Aldicarb), S-methyl N-[methylcarbamonyl(oxy)]thioacetamine (lannate), chlorinated camphene, 67 percent octachlorocamphene (Toxaphene), tricalcium aresenate, sodium aluminum fluoride, Dichlorodiphenyltrichloroethane, tricyclohexyltin hydroxide (Plictran), and combinations thereof; wherein said Nematicide is selected from the group consisting of O,O-diethyl-O-2,4-dichlorophenyl phosphorothioate (dichlofenthion), O-ethyl S,S-dipropyl phosphorodithioate (Ethoprop), and combinations thereof; wherein said molluscicide is selected from the group consisting of copper sulfate, n-tritylmorpholine (trifenmorph), tributyltin fluoride, sodium pentachlorophenate, and combinations thereof; wherein said herbicide is selected from the group consisting of 2,4-dichlorophenoxyacetic acid (2,4-D), alkylamine salts of 2,4-D, butoxyethanol ester of 2,4-D, 2,4,5-trichlorophenoxyacetic acid (2,4,5-T), 2-(2,4,5-trichlorophenoxy)priopionic acid (Silvex), 3-amino-2,5-dichlorobenzoic acid (chloramben), 3,6-dichloro-O-anisic acid (Dicamba) 2,3,5-trichlorophenylacetic acid (Fenac), 2,6-dichlorobenzonitrile (Dichlobenil), N,N-diallyl-2-chloroacetamine (Randox) S-ethyl diisobutylthiocarbamate (Sutan), isopropyl N-(3-chlorophenyl) carbamate (chloropropham), 3-amino-1,2,4-triazole (Amitrole), 2-chloro-4,6-Bis(ethylamino)-isopropylamino-S-triazine (Atrazine), and combinations thereof; and, wherein said fungicide is selected from the class consisting of triphenyltin acetate, methyl-1-(butacarbamoyl)-2-benzimidazole carbamate (Benomyl), and combinations thereof.

71. A solution according to claim 70, wherein said solvent is selected from the group consisting of alcohols having from 1 to 5 carbon atoms, acetone, diisobutyl ketone, methyl ethyl ketone, dioxane, methylene chloride, water, and combinations thereof.

72. A solution according to claim 71, wherein the amount of said polymer ranges from about 4 percent to about 13 percent by weight, wherein the amount of said solvent ranges from about 50 percent to about 90 percent by weight, and wherein the amount of said particle ranges from about 5 percent to about 30 percent by weight.

73. A solution according to claim 72, wherein said adhesive agent has the formula

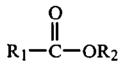

wherein $R_1$ and $R_2$ have from 2 to 5 carbon atoms, and the amount of said adhesive agent ranges from about 0.01 to about 3 percent by weight based upon the total weight of said solution.

74. A solution according to claim 73, wherein said solvent is selected from the group consisting of water, an alcohol having from 1 to 5 carbon atoms, and combinations thereof.

75. A solution according to claims 65, 67, 68, 70, 72, or 73, wherein said polymer is said polyvinyl acetate.

76. A solution according to claims 65, 67, 68, 70, 72, or 73, wherein said polymer is said polyvinyl ether.

77. A solution according to claim 76, wherein said polyvinyl ether has two carbon atoms in the repeating group.

78. A solution according to claims 65, 67, 68, 70, 72, or 73, wherein said polymer is said acrylic polymer or copolymer.

79. A solution according to claim 78, wherein $R_4$ of said formulation is hydrogen or an alkyl having from 1 to 4 carbon atoms, and wherein said $R_5$ of said formula is hydrogen or an alkyl having from 1 to 3 carbon atoms, and wherein the molecular weight of said polymer or said copolymer ranges from about 30,000 to 300,000.

80. A solution according to claims 65, 67, 68, 70, 72, or 73, wherein said polymer is said interpolymer.

* * * * *